(12) United States Patent
Laughlin

(10) Patent No.: US 9,134,284 B1
(45) Date of Patent: *Sep. 15, 2015

(54) REMOTE GAS SAMPLE ANALYSIS AND MONITORING SYSTEM

(75) Inventor: Robert M. Laughlin, Miramar, FL (US)

(73) Assignee: Lawrence Factor, Inc., Miami Lakes, FL (US)

( * ) Notice: Subject to any disclaimer, the term of this patent is extended or adjusted under 35 U.S.C. 154(b) by 168 days.

This patent is subject to a terminal disclaimer.

(21) Appl. No.: 13/271,473

(22) Filed: Oct. 12, 2011

Related U.S. Application Data

(60) Continuation-in-part of application No. 11/677,676, filed on Feb. 22, 2007, now Pat. No. 8,038,948, which is a division of application No. 10/045,229, filed on Nov. 9, 2001, now Pat. No. 7,183,115.

(51) Int. Cl.
   *G01N 31/00* (2006.01)
   *G01N 31/22* (2006.01)

(52) U.S. Cl.
   CPC .............. *G01N 31/00* (2013.01); *G01N 31/224* (2013.01); *G01N 31/223* (2013.01)

(58) Field of Classification Search
   CPC .... G01N 31/00; G01N 31/223; G01N 32/224
   USPC ............. 422/83; 436/38, 60, 181; 702/22–24; 73/31.01–31.03
   See application file for complete search history.

(56) References Cited

U.S. PATENT DOCUMENTS

| | | | |
|---|---|---|---|
| 4,459,266 A * | 7/1984 | Lamoreaux | 422/86 |
| 5,521,845 A | 5/1996 | Ukon et al. | |
| 5,835,871 A | 11/1998 | Smith et al. | |
| 6,033,457 A | 3/2000 | Lawless | |
| 6,466,133 B1 | 10/2002 | Skardon | |
| 6,604,033 B1 | 8/2003 | Banet et al. | |
| 6,606,566 B1 | 8/2003 | Sunshine | |
| 6,631,333 B1 | 10/2003 | Lewis et al. | |
| 2002/0144537 A1 | 10/2002 | Sharp et al. | |
| 2002/0152037 A1 | 10/2002 | Sunshine et al. | |
| 2003/0216869 A1 | 11/2003 | Sunshine | |

OTHER PUBLICATIONS

Richard W. Walker, "Nevada gets new emissions data system", Government Computer News, Jul. 1997 at http://www.gcn.com/archives/sl/1997/July/covl.htm (copyright 1999 by Post-Newsweek Business Information, Inc.).

* cited by examiner

*Primary Examiner* — Jan Ludlow
(74) *Attorney, Agent, or Firm* — Malin Haley DiMaggio & Bowen, P.A.

(57) ABSTRACT

A gas analyzer system for analyzing and monitoring samples of compressed or ambient gas such as breathing air and informing the user as to the results of the sample's gas purity without the gas sample having to be physically transported to an accredited laboratory. The system comprises a gas analysis module situated at a user facility for receiving the contents of a gas sample and detecting gas impurity characteristics, and a server situated at a remote certification and monitoring center and electrically coupled to the gas analysis module via a bi-directional communications link such a computer network connection. The remote server receives and stores the gas purity characteristics in the form of computer-readable gas impurity data obtained from the analysis module. The server compares the impurity data with the contents of a database containing threshold gas purity parameters and provides the test results to the user facility by electronic messaging.

17 Claims, 3 Drawing Sheets

REMOTE GAS SAMPLE ANALYSIS AND MONITORING SYSTEM

CROSS REFERENCE TO RELATED APPLICATIONS

This application is a continuation-in-part of U.S. patent application Ser. No. 11/677,676 filed Feb. 22, 2007, which is a divisional application of U.S. patent application Ser. No. 10/045,229, filed Nov. 9, 2001, now U.S. Pat. No. 7,183,115.

BACKGROUND OF THE INVENTION

1. Field of the Invention

The invention generally relates to a gas purity analysis and monitoring system, and particularly to a system capable of analyzing a gas sample at a user facility and transmitting gas purity and/or oil and particle information to a remote facility where it is quickly determined if the gas substance has passed certain gas purity requirements. The remote facility is also capable of providing continuous and automatic monitoring services with respect to gas purity and/or oil and particle levels.

2. Description of the Prior Art

There is a growing need in the industry for gas purity testing systems that can provide gas purity analysis results to the user quickly and efficiently. The standard method in the art for testing the quality of gas samples is to first capture the sample and then transport the actual sample to a certified, accredited laboratory for analysis. The user must then wait, weeks perhaps, until the sample has been analyzed and certified by a qualified government laboratory.

However, given the demand for quality air sources, such as compressed air tanks for SCUBA diving, and compressed air used for human inhalation in industrial plants, hospitals and by firemen, as well as ambient air, the standard method is not practical. It is cumbersome and costly, given the potential loss of sales a vendor may experience waiting for certification of the gas sample. These samples often must be taken periodically at short time intervals which further exacerbates the problem.

Further, a gas sample that passes the required gas purity standards and obtains certification one day may, if impurities enter the tank or facility, become tainted and fall below the certification requirement the next day. However, given the length of time and cumbersome nature of transporting gas sample to a test center, the facility, possibly a hospital, will rely on its prior certification, leading to a possibly dangerous, if not life-threatening situation wherein air, believed to be pure based upon a prior, three-week-old test, actually contains impurities.

Accordingly, there is a significant need in the art for a gas purity sample analysis system that allows a user to effectively test an air sample on site as often as the user would like and without the actual sample being physically carried to a testing facility, while still being certified by a qualified third party, by providing the gas sample into a sampling unit located at the user's facility, and the results being electrically transmitted remotely to the certification facility. The gas purity and/or oil/particle content information is then sent, via electronic data transmission, to a monitoring center where the sample quality information is compared by qualified people to a database of industry standards, and the user is notified, within minutes, if the sample tested has attained certification by meeting or exceeding industry purity standards. Further, there is a need in the art for a gas purity analysis system whereby the remote facility can constantly monitor the gas supply at a user facility and send instructions and/or shut down the flow of gas should be determined to be contaminated.

It is, therefore, to the effective resolution of the aforementioned problems and shortcomings of the prior art that the present invention is directed.

SUMMARY OF THE INVENTION

The present invention provides a gas sample quality analysis system for analyzing, monitoring, and certifying samples of gas and/or breathing air substances, including compressed gasses, comprising a gas analysis module situated on site at a user facility for capturing a real time sample of a gas. The gas analysis module is capable of detecting gas impurity characteristics of a given sample and can convert the gas impurity characteristics into computer-readable data, wherein the data is representative of the gas impurity characteristics. The module can transmit, over a bi-directional computer network-based communications link, the gas impurity data to a computer server situated at a gas certification and monitoring center, whereby the server contains a data storage component for identifying the sample being tested and for storing the gas impurity data, and computer instructions capable of determining if the gas sample passes certain gas purity requirements. The module can also transmit other data and instructions, including but not limited to, identification data, configuration data, status data, and the like. The data transmission system may be any form of data transmission including but not limited to both hard-wired and wireless, and, preferably is accomplished via a computer Internet connection. In some embodiments, the data analysis site is a government-approved facility that is qualified to certify the quality of gas samples.

In some embodiments, the gas certification and monitoring center is also capable of sending messages and instructions back to the gas analysis module over the bi-directional communications link. Accordingly, in one embodiment of the present invention, the gas analysis system further comprises a data certification component for informing a user if the gas sample has passed the gas purity requirements. This could be in the form of an electronic or printed message. In another embodiment, test results are stored and/or printed at a qualified monitoring center, which is an accredited gas purity testing laboratory, or at another location. If the samples are acceptable, the gas quality is certified and the user notified electronically. In yet other embodiments, the gas certification and monitoring center can send, via the server over the bi-directional communications link, instructions to the gas analysis module at the user facility such as, for example, to shut down the system, or alert individuals at the user facility that the gas is contaminated.

The gas analysis module comprises at least a gas collection compartment for collecting and temporarily storing the gas sample, a plurality of gas impurity sensors capable of generating gas impurity signals corresponding to gas impurity characteristics detected thereby, a data processing chip set for converting the detected gas impurity signals into computer-readable gas impurity data, and a communications device for establishing a bi-directional communications link capable of transmitting the computer-readable data to the gas certification and monitoring center and receiving instructions and/or messages from the monitoring facility. The module may also include a display and one or more status lights.

In some embodiments, the gas purity sensors comprise infrared, electro-chemical and color metric for detecting gas impurities in the gas sample. In some embodiments, the gas analysis module is disposed between a gas source, such as an air compressor, and a gas storage and/or filling tank. Accordingly, the gas is analyzed for impurities prior to entering the storage tank, allowing the user facility to dispose of contaminated gas before it enters an individual's personal scuba or air tank.

To utilize the present invention, a user installs the gas analysis module at the user facility, preferably between a gas source and a gas collection tank/unit. The gas analysis module then establishes a bi-directional communications link with a remote server at the gas certification and monitoring center by way of the module's integrated communications device, which may be wired or wireless. Typically, the bi-directional communications link will be established over the Internet or other similar communications network. Having established the communications link, the user facility then notifies the gas certification and mentoring center that the user needs to begin testing a gas sample. This notification may be accomplished by sending a message from the module to the remote server automatically, or by placing a call or sending an external message from the user facility to the monitoring center. The gas certification and monitoring center confirms that the communications link has been established and informs the user facility that testing may begin. At that point, gas flow into the analysis module is initiated, and the sensors within the module begin detecting gas impurities. Sensor signals are converted by the chipset within the module into computer readable data, which data is transmitted from the module to the gas certification and monitoring center over the bi-directional communications link. At that point, the monitoring center can interpret the data and provide the results to the user facility.

Upon receipt of the gas impurity data, the server controlled by the certification and monitoring center stores this information and compares the data to the contents of a reference database containing gas purity threshold parameters to determine if the gas sample passes one or more gas purity requirements for certification and fitness for use/consumption. The results of the comparison (i.e. positive or negative) are sent back to the user facility from the monitoring center. This notification could be in the form of a return e-mail or fax, which is automatically forwarded to the user. Alternatively, the server can send a message over the bi-directional communications link directly to the analysis module, which message can be displayed on the module's display or status lights. Further, the monitoring center can also transmit instructions to the module over the bi-directional communications link, such as to power down the device in the event of imminent contamination. In either case, the user, without having to transport the sample to an accredited facility or laboratory, is informed, usually within minutes, as to the success or failure of the gas purity test, performed by a certified testing center.

In a preferred embodiment of the present invention, an improved machine is provided that allows a user to test and receive third party certification of an gas sample for both gas and oil impurities without having to physically transfer the real time gas sample to a certified remote facility.

It is therefore an object of the invention to provide a gas analysis system that eliminates the need for a user to physically transport a gas sample to a certification facility for gas purity testing.

It is another object of the invention to provide a gas analysis system that reports to the user the success or failure of the gas purity test within minutes by a third party, certified, qualified entity approved by the government.

It is yet another object of the invention to provide a gas analysis system that provides the user with a printed and/or electronic message informing the user of the success or failure of the gas purity test.

It is still another object of the invention to provide a gas analysis system that detects the existence of oil particle impurities within the gas sample and can get remote certification as to the particulates.

It is still another object of the invention to provide a gas analysis system adapted to provide continuous and automatic remote monitoring of gas impurities and oil particle content by a certified third party monitoring center.

In accordance with these and other objects which will become apparent hereinafter, the instant invention will now be described with particular reference to the accompanying drawings.

DESCRIPTION OF THE PREFERRED EMBODIMENTS

Figure 1:
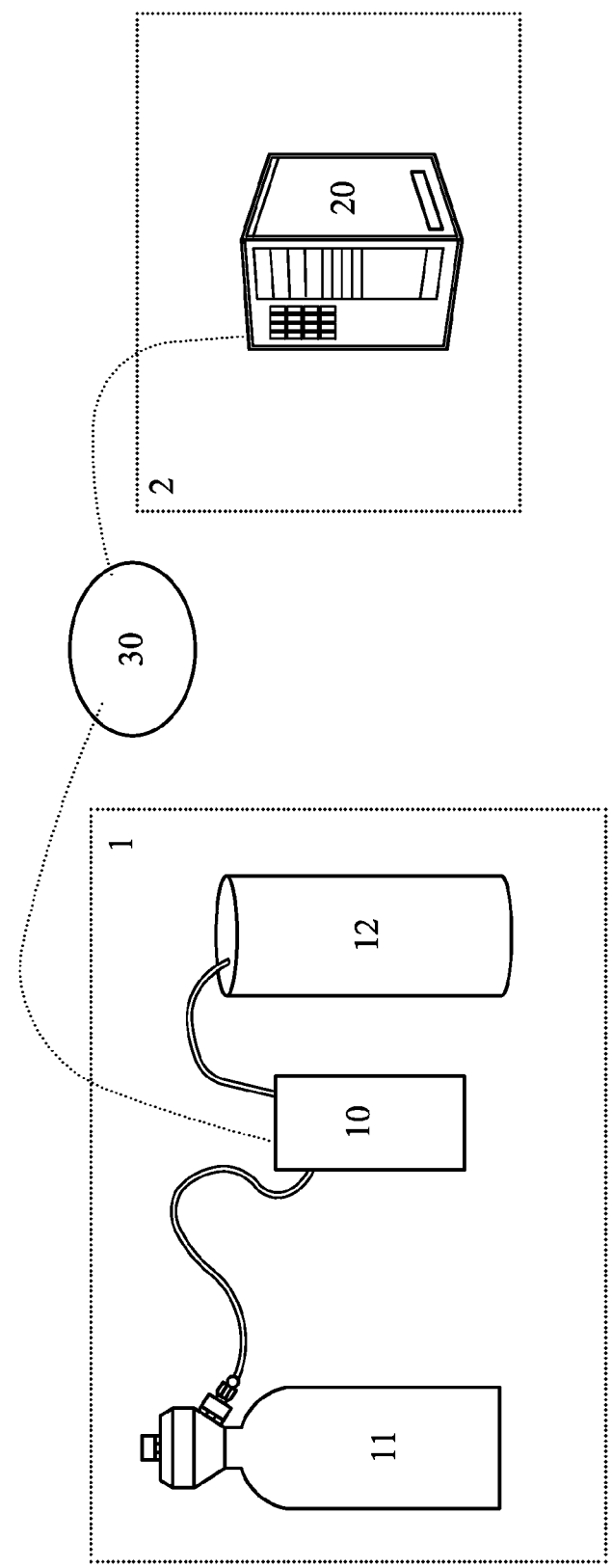
FIG. 1 is a schematic of the components of the gas sample analyzing system of the present invention.

FIG. 1 is a schematic of the remote gas analysis system of the present invention. At the user facility 1, the system includes a gas analysis module 10 disposed between a gas source 11 and a gas collection tank 12. It is appreciated that the gas source 11 may include, without limitation, a compressor or other similar gas-providing system. The gas collection tank may include, without limitation, a storage tank used to fill smaller personal gas tanks or breathing tanks. Alternatively, the module 10 may be directly removably connected to such a personal gas tank or breathing tank. Further still, the analysis module 10 could be integrated into a compressor or other gas source, it being understood that the module receives gas downstream from the source, i.e. after the compressor's outlet. Thus, while the figures herein show module 10 as a discrete component, such figures are merely illustrative; the module 10 can be integrated into any gas handling device wherein gas quality analysis is desired.

At the gas certification and monitoring center 2, the system further includes a server 20. A bi-directional communications link between module 10 and server 20 is established over computer network 30 which may be, for example, the Internet.

Figure 2:
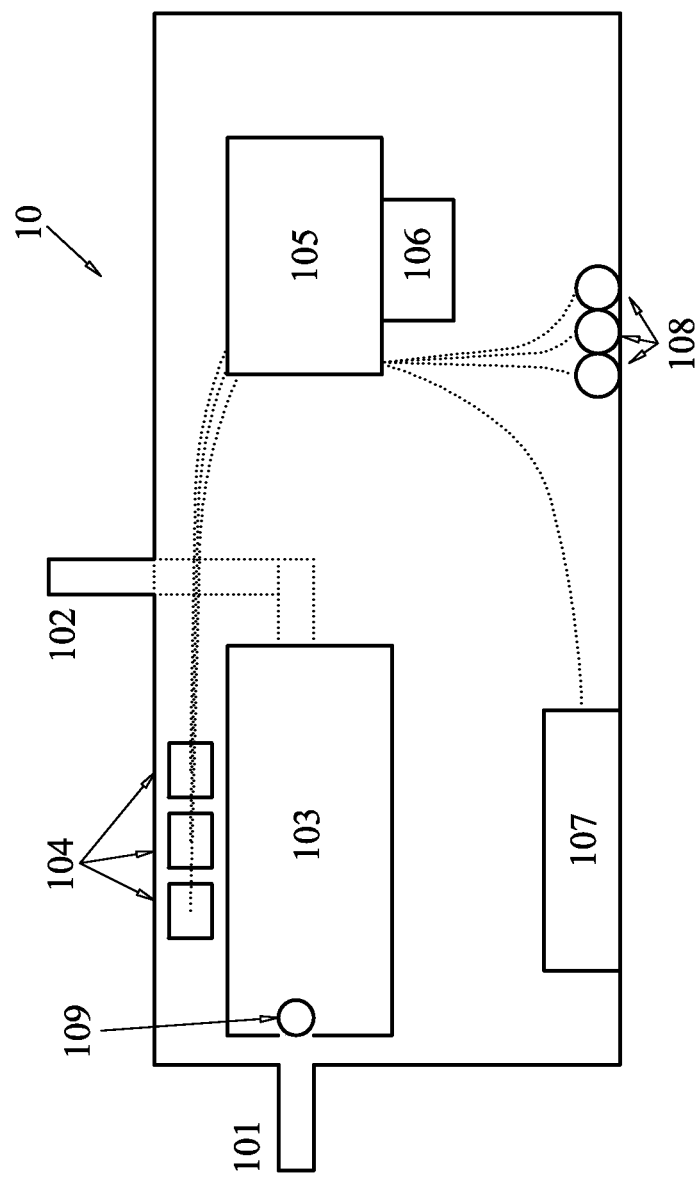
FIG. 2 is a schematic representation of the gas analysis module of the present invention.

With reference to FIG. 2, shown is a schematic of one embodiment of the gas analysis module 10 of the present invention. Module 10 includes a gas inlet 101 and a gas outlet 102. Gas compartment 103 is disposed between and in fluid flow communication with inlet 101 and outlet 102 and is adapted to temporarily contain a sample of gas to be tested for impurities. Each of the inlet 101 and outlet 102 may include appropriate gas line fittings as are known in the art, such that they are compatible with the fittings of the gas source 11 and gas collection tank 12, respectively. Inlet 101 and outlet 102 may also include valves operable to open and close the inlet 101 and outlet 102 as desired. The arrangement also provides a passageway for gas to be transported from a gas source 11 to a collection tank 12. An electronic flow detector 109 may be in flow communication with inlet 101 and is adapted to detect a change in pressure, flow rate, and/or temperature such that the module 10 can be activated immediately when gas is introduced into the module, rather than rely on a user to manually activate the module 10.

One or more gas sensors 104 are in fluid communication with the gas passing through compartment 103. In some embodiments, the gas sensors 104 are electronic UV or ionic gas sensors capable of generating an electronic signal based on various gas impurity characteristics. In some embodiments, the electronic signal corresponds to a voltage or electronic potential. The gas sensors 104 can be calibrated to detect virtually any type of gas impurity. The following is a non-exhaustive list of gas impurities the present inventions is capable of detecting. This list is illustrative only and is set forth here merely to give a broad understanding of the some of the impurities recognized:

Analytes
Carbon Dioxide
Carbon Monoxide
Hydrocarbons
Water Vapor
Nitric Oxide
Sulfur Dioxide
Halogenated Solvents
Acetylene
Halogenated Hydrocarbons
Oil and Particles
Oxygen
Nitrogen Dioxide
Odor The gas sensors 104 are electrically coupled to chipset 105 of module 10. Chipset 105 includes the necessary electronic and computing components to receive gas impurity electronic signals from the sensors 104 and convert the electronic signals to computer readable gas impurity data. Chipset 105 may include, without limitation, a computer processor, a storage component (i.e. a hard driver or other storage medium), read-only memory (ROM), random access memory (RAM), a plurality of inputs and outputs, and one or more analog-to-digital converters. The chipset 105 may also be configured with software to provide the necessary operational functionality for the module 10. Accordingly, in some embodiments, chipset 105 receives analog electronic signals from sensors 104 and passes the signals through its analog-to-digital converters, resulting in digital computer readable impurity data.

Chipset 105 is further in electrical communication with communication device 106. In some embodiments, communication device 106 provides a wired or wireless connection to a computer network, such as the Internet or an intranet. Accordingly, communication device 106 may comprise, without limitation, a wired Ethernet modem, a telephone modem, a wireless internet (Wi-Fi) device, a wireless cellular device (CDMA, GSM, etc. . . . ), and the like. Communication device 106 is capable of receiving the computer readable impurity data from chipset 105 and sending the data over a computer network, such as the aforementioned Internet and/or a local intranet. Chipset 105 is also in electrical communication with display 107 and one or more status lights 108. Display 107 can display messages concerning the module's status and gas impurity data as well as provide an interface for setting up the module. Status lights 108 can be configured to show power status, communications status, impurity status (for example, green if the gas composition is clean, red if unhealthy levels of impurities are detected).

Further, it is appreciated and understood that the physical configuration of module 10 can vary depending on the desired installation and application. FIG. 2 merely represents a schematic of the various components of module 10 and the instant disclosure should not be construed as limiting module 10 to a particular physical layout and configuration.

With reference again to FIG. 1, module 10 establishes a connection to computer network 30 via communication device 106, either wired or wirelessly. Module 10 utilizes the computer network 30 to establish a bi-directional communications link with server 20 located at a remote gas certification and monitoring center 2. Accordingly, in some embodiments, server 20 is a computing system including, without limitation, a computer processor, a data storage component (i.e., a hard drive or other storage medium), read-only memory (ROM), random access memory (RAM), a plurality of inputs and outputs, and a communication device. The communication device of the server enables the server to connect to computer network 30 (i.e. the Internet and/or an intranet) and, in turn enabling the bi-directional communications link with module 10.

Figure 3:
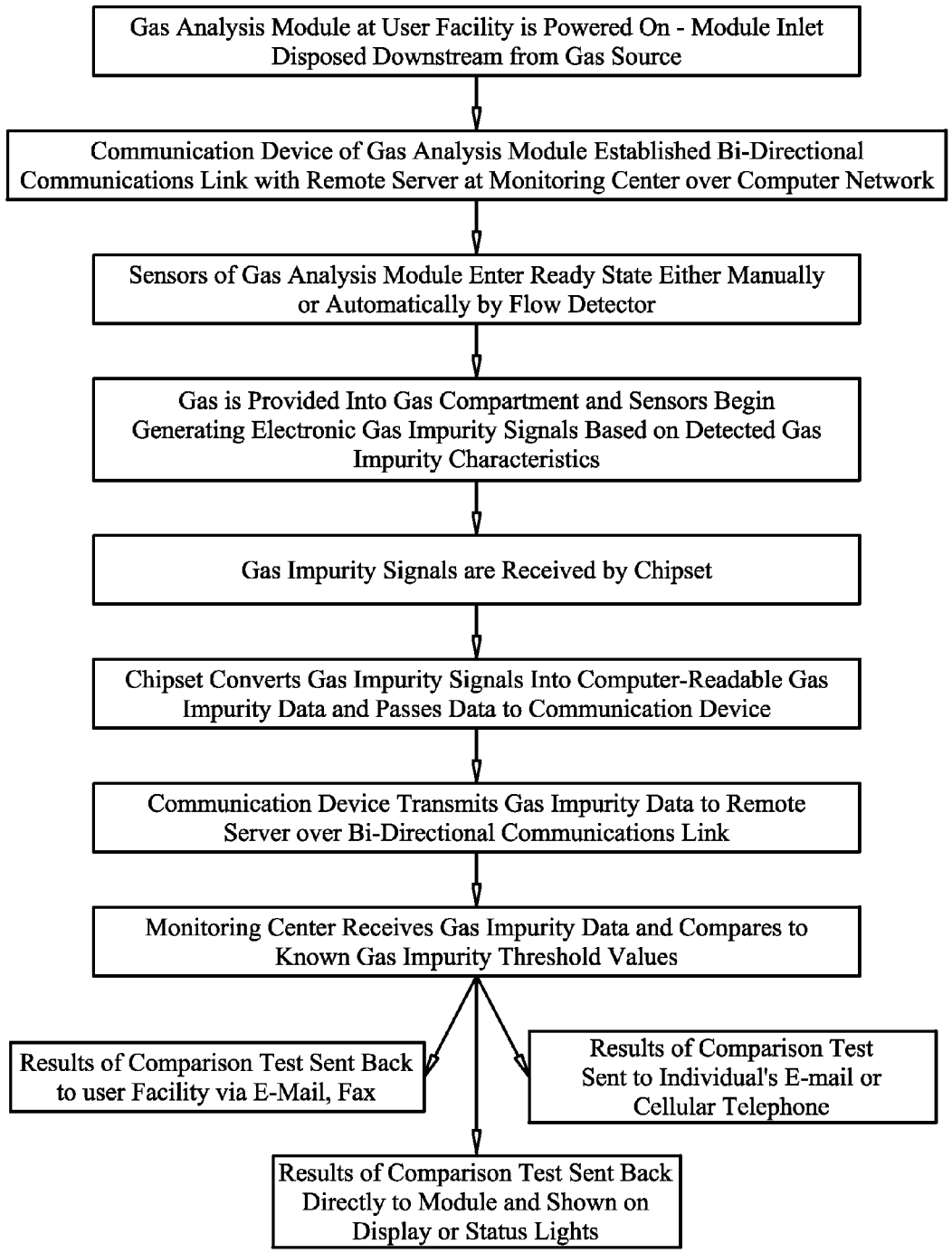
FIG. 3 is a flow chart depicting the system and method of the present invention.

With reference to the flow chart shown in FIG. 3, in use, the system of the present invention enables remote gas analysis and continuous monitoring of gas impurities of a given gas source 11. At the user facility 1, the analysis module 10 is powered on and the communication device 106 connects to computer network 30. Communication device 106 utilizes computer network 30 and sends instructions to server 20 located at the remote gas certification and monitoring center 2, whereby the bi-directional communications link is established. At the same time, sensors 104 are activated and enter a "ready" state. The sensors 104 can be activated manually or, alternatively, sensors 104 enter a "ready" state upon receiving the appropriate signal from the flow detector 109 at the inlet 101 of the module 10, i.e. sensors 104 are automatically activated upon the introduction of gas into the module 10.

In any event, gas to be analyzed is provided from the gas source 11 into the compartment 103 of module 10. As gas enters compartment 103 it comes in contact with sensors 104. Accordingly, sensors 104 begin detecting gas impurity characteristics of the provided gas and generate electronic gas impurity signals corresponding to the gas impurity characteristics, which signals are received by chipset 105. Chipset 105 converts the gas impurity signals into computer-readable gas impurity data and passes the data to communication device 106. Communication device 106 transmits the gas impurity data to server 20 at the remote gas certification and monitoring center 2 over the already established bi-directional communications link.

Once at the monitoring center 2, a qualified representative receives the gas impurity data and compares the impurity data to a known preexisting list of gas impurity threshold values to determine if a specific gas impurity level has been exceeded and/or to determine if the gas sample passes one or more gas purity requirements for certification. The results of the comparison test are then determined, the information stored under the name of the user, and the test results sent back to the user facility 1 or an individual, either by an electronic message, or via a fax or paper delivery. To that end, the monitoring center 2 can send information and messages directly back to the analysis module 10 over the bi-directional communications link. Such messages, including test results, are received by communication device 106, processed by chipset 105, and then may be displayed on display 107 of the module or be represented by a particular status light 108. Alternatively, the monitoring center 2 can send an external message, such as test results, to an e-mail inbox (e.g. the user facility's e-mail inbox, or a manager's persona e-mail inbox), a cellular telephone (e.g. via text message), or other electronic message receiving device. Of course, the monitoring center 2 could send a plurality of message simultaneously, for example, directly to module 10 for instant feedback and to the user facility manager's e-mail inbox for storage and recordation. In some embodiments, the monitoring center 2 can send an electronic certificate showing compliance with various gas purity standards is transmitted. The certificate could be sent via electronic mail or other electronic messaging means separate from the analysis module, (i.e. to the e-mail inbox of a computer at the user facility 1 or an individual's cell phone or e-mail account). A certificate may be desired because the user facility 1 can then display it to customers to assure compliance and gas purity.

Further, the server 20 at the monitoring center 2 can send, over the bi-directional communications link, a variety of instructions to analysis module 10. For example, if an extremely high level of impurities is detected, the monitoring center 2 can send a "shut down" instruction to the module 10, which would close the inlet 101 and outlet 102, preventing further flow and/or collection of contaminated gas. The monitoring center 2 can also send calibration instructions to the module 10, to assure that the sensors 104 and other components are properly calibrated and functioning correctly. The monitoring center 2 can also send configuration instructions to the module 10, to enable the module 10 to properly and efficiently operate on the bi-directional communications link. Further yet, the monitoring center 2 can send software and firmware updates to the module 10 to assure the most up-to-date functionality of the system. Thus, the server of the monitoring center 2 is capable of transmitting instructions including, but not limited to, power down instructions, calibration data, configuration data, software data, and combinations thereof.

The analysis module 10 may include a unique identifier such as an IP address or the like which allows the monitoring center 2 to identify the location and characteristics of a particular module 10. In some embodiments, the unique identifier is built into the module 10 prior to receipt by the user facility 1. In some embodiments, after the module 10 has been appropriately installed at the user facility 1, the user facility 1 informs the monitoring center 2 that it wishes to configure the module 10 for future testing and monitoring. The module 10 then establishes its connection with the computer network 30 (i.e. the Internet and/or Intranet) and then the monitoring center 2 can connect to the module 10 by utilizing the unique identifier. In some embodiments, once the initial configuration process has been completed, the module 10 is capable of automatically establishing the bi-directional communications link with the server 20 at the monitoring center 2 without additional action. Accordingly, the module 10 at the user facility 1 can automatically begin sending impurity data to server 20 at the monitoring center 2, whereby the monitoring center 2 can automatically provide test results. This avoids the step of having to inform the monitoring center 2 that the user facility 1 wishes to conduct a test. In other words, the user facility 1 can conduct testing "on demand" and at its discretion by way of the dynamic and continuous bi-directional communications link.

To that end, it is appreciated that the bi-directional communications link between module 10 and server 20 can be maintained for extended periods of time so that the gas certification and monitoring center 2 can monitor gas impurity data automatically and continuously. Thus, the flow detector 109 at the inlet 101 of the module 10 is particularly useful as it will activate the sensors 104 and other module 10 components upon the detection of gas flow and can likewise deactivate the sensors 104 and module 10 components if no gas flow is detected, thus saving energy. These automated capabilities reinforce the "on-demand" testing and continuous monitoring features of the present invention. Monitoring is particularly useful where the user facility 1 is quite active and carries out a large number of filling operations in a single day. Of course, if on-demand and/or automated testing is not desired, the module 10 can operate in manual mode wherein it only sends instructions and impurity data to server 20 at the monitoring center 2 upon user manipulation and/or instruction. The monitoring capabilities of the present invention provides a significant improvement over the prior art in that user facility can determine the viability of its gas and/or air supply at all times, rather than at weekly or monthly intervals.

The present invention provides expedited gas analysis where the sample is gathered and kept at the user facility 1, is tested at the user facility 1 and is certified for safety remotely by qualified gas analysis experts without having to physically transport the actual gas sample from the user facility 1 to a qualified laboratory. It is appreciated the user facility 1 may be a dive shop with SCUBA equipment, a hospital or fire station, or a large industrial plant containing ambient or compressed air that needs to be analyzed and certified as safe. The sample to be tested could be compressed air to be provided in a SCUBA tank or firefighter's breather apparatus, a sample of ambient air, or a sample of oxygen provided to patients in a hospital setting.

The instant invention has been shown and described herein in what is considered to be the most practical and preferred embodiment for an example helicopter drive train. It is recognized, however, that departures may be made therefrom within the scope of the invention and that obvious modifications will occur to a person skilled in the art.

What is claimed is:

1. A remote breathing air analysis and monitoring system comprising:

A bi-directional computer network that includes the internet comprising a user facility that provides air for filling compressed air breathing tanks;

a compressed air source at said user facility for filling breathing tanks;

an air analysis module situated at said user facility to receive continuously a compressed breathing air sample from said compressed air source, detect gas impurity characteristics of said sample, convert said compressed breathing air impurity characteristics into computer-readable breathing air impurity data, and transmit said computer-readable gas impurity data over said bi-directional computer network;

a compressed breathing air certification center and monitoring center;

a server maintained by said compressed breathing air certification and monitoring center, said server having a data receiver to receive said computer-readable breathing air impurity data over said computer network;

said server including a computer to compare said breathing air impurity data to one or more compressed breathing air purity threshold parameters to determine continuously if said compressed breathing air sample passes one or more gas purity requirements for certification by said compressed remote breathing air certification and monitoring center; and said server connected to said computer network to transmit one or more messages to said user facility concerning said compressed breathing air purity requirements.

2. The system of claim 1, wherein said compressed breathing air analysis module comprises:

an inlet receiving continuously said compressed breathing air sample from a compressed breathing air supply source;

a compressed breathing air compartment in flow communication with said inlet;

a plurality of compressed breathing air sensors in fluid communication with said compartment, said sensors capable of detecting said compressed breathing air impurity characteristics of said sample and generating compressed breathing air impurity signals corresponding to said compressed breathing air impurity characteristics;

a chipset;

a communication device in electrical communication with said chipset;

wherein said breathing air sensors are electrically coupled to said chipset, said chipset receiving said compressed breathing air impurity signals and converting said compressed breathing air impurity signals into said computer-readable compressed breathing air impurity data; and said communication device receiving said computer-readable breathing air impurity data from said chipset and transmits said data to said server over said computer network.

3. The system of claim 2, wherein said communication device is wireless.

4. The system of claim 1, wherein said server is connected to said computer network, to transmit one or more messages concerning said compressed breathing air purity requirements to said compressed breathing air analysis module, said module displaying said messages on a display at predetermined times.

5. The system of claim 1, wherein said server is connected to said computer network, to transmit one or more messages concerning said compressed breathing air purity requirements to said compressed breathing air analysis module, said module displaying said messages on one or more status lights.

6. The system of claim 1, wherein said server is connected to said computer network, to transmit one or more instructions to said compressed breathing air analysis module.

7. A method of remotely analyzing a supply of compressed breathing air continuously, comprising the steps of:

establishing a bi-directional communication link between a compressed breathing air analysis module at a user facility and a server at a remote breathing air certification and monitoring center;

providing said compressed breathing air analysis module at said user facility, with a sample of compressed breathing air for testing;

detecting, within said compressed breathing air analysis module, one or more compressed breathing air impurity characteristics of said sample;

converting, on said compressed breathing air analysis module, said one or more compressed breathing air impurity characteristics of said sample into computer-readable compressed breathing air impurity data;

transmitting said computer-readable compressed breathing air impurity data continuously to said server over said bi-directional communications link; and receiving continuously, from said server, the results of a comparison of said computer-readable compressed breathing air impurity data to one or more purity threshold parameters which comparison determines if said sample passes one or more compressed breathing air purity requirements for certification by said remote compressed breathing air certification and monitoring center.

8. The method of claim 7, wherein said results are received by said analysis module over said bi-directional communications link.

9. The method of claim 8, wherein said results are displayed on a display of said analysis module.

10. The method of claim 8, wherein said results are displayed on one or more status lights of said analysis module.

11. The method of claim 7, wherein said results are received as an electronic mail message.

12. The method of claim 7, wherein said results are received as an electronic message on a cellular telephone.

13. The method of claim 7, further including the step of receiving, on said analysis module from said server over said bi-directional communications link, one or more instructions.

14. The method of claim 13, wherein said instructions comprise power down instructions, calibration data, configuration data, software data, and combinations thereof.

15. The method of claim 7, wherein said compressed breathing air analysis module comprises:

an inlet receiving said compressed breathing air sample continuously from a breathing air supply source;

a compressed breathing air compartment in flow communication with said inlet;

a plurality of compressed breathing air sensors in fluid communication with said compartment, said sensors capable of detecting said breathing air impurity characteristics of said sample and generating breathing air impurity signals corresponding to said gas impurity characteristics;

a chipset;

a communication device in electrical communication with said chipset;

wherein said breathing air sensors are electrically coupled to said chipset, said chipset receiving said impurity signals and converting said breathing air impurity signals into said computer-readable impurity data;

wherein said communication device receives said computer-readable compressed breathing air impurity data from said chipset and transmits said data to said server over said bi-directional communications link.

16. The method of claim 15, wherein said communication device is wireless.

17. The method of claim 7, wherein said bi-directional communications link is established over the Internet.

* * * * *